United States Patent [19]

Tepper

[11] Patent Number: 5,376,001
[45] Date of Patent: Dec. 27, 1994

[54] REMOVABLE ORTHODONTIC APPLIANCE

[76] Inventor: Harry W. Tepper, 535 Ocean Ave., #2B, Santa Monica, Calif. 90402

[21] Appl. No.: 58,374

[22] Filed: May 10, 1993

[51] Int. Cl.⁵ .................................................. A61C 3/00
[52] U.S. Cl. .................................................. 433/6
[58] Field of Search ........................... 433/6, 7, 18, 24

[56] References Cited

U.S. PATENT DOCUMENTS

| | | | |
|---|---|---|---|
| 1,582,570 | 4/1926 | Brust | 433/7 |
| 3,162,948 | 12/1964 | Gerber | 433/7 |
| 3,174,851 | 3/1965 | Buehler et al. | |
| 3,351,463 | 11/1967 | Rozner et al. | |
| 3,454,001 | 7/1969 | Stockfisch | 433/6 |
| 4,028,808 | 6/1977 | Schwartz | 433/7 |
| 4,416,626 | 11/1983 | Bellaria | 433/7 |
| 4,424,031 | 1/1984 | Dahan | |
| 4,433,956 | 2/1984 | Witzig | |
| 4,468,196 | 8/1984 | Keller | |
| 4,752,222 | 6/1988 | Bass | 433/6 X |
| 4,976,614 | 12/1990 | Tepper | |
| 5,096,416 | 3/1992 | Hulsink | 433/6 |
| 5,167,499 | 12/1992 | Arndt et al. | 433/7 |

FOREIGN PATENT DOCUMENTS 990685 9/1951 France .................................. 433/7
1101 of 1869 United Kingdom .................. 433/7

Primary Examiner—Gene Mancene
Assistant Examiner—Nicholas D. Lucchesi
Attorney, Agent, or Firm—Gordon K. Anderson

[57] ABSTRACT

A removable orthodontic appliance which has a labial arch wire (20), continuous with a patient's anterior teeth surfaces, that is connected to a pair of clasps (32) seated over several midregion teeth. A pair of structural braces, either molded wings (36) or connecting sections (50), attach the clasps to a lingual arch wire (38) that is made of memory metal to optimize the force of the arch shape on the connected teeth. A bridge, formed by a radial loop (42), is connected between the braces and exerts persistent linear force to the teeth in the opposite direction of deformation. The loop is also preferably made of memory metal and has a constant tendency to return to its original shape, thus controllably effecting the desired tooth relocation. Another embodiment utilizes a number of radial arcs (56) between the molded wings that are placed angularly to not only move the teeth laterally, but retain an angular relationship with the roots of the teeth relative to the patient's basal bone structure. This method non-surgically reshapes the alveolar bone in which the posterior teeth are supported.

19 Claims, 3 Drawing Sheets

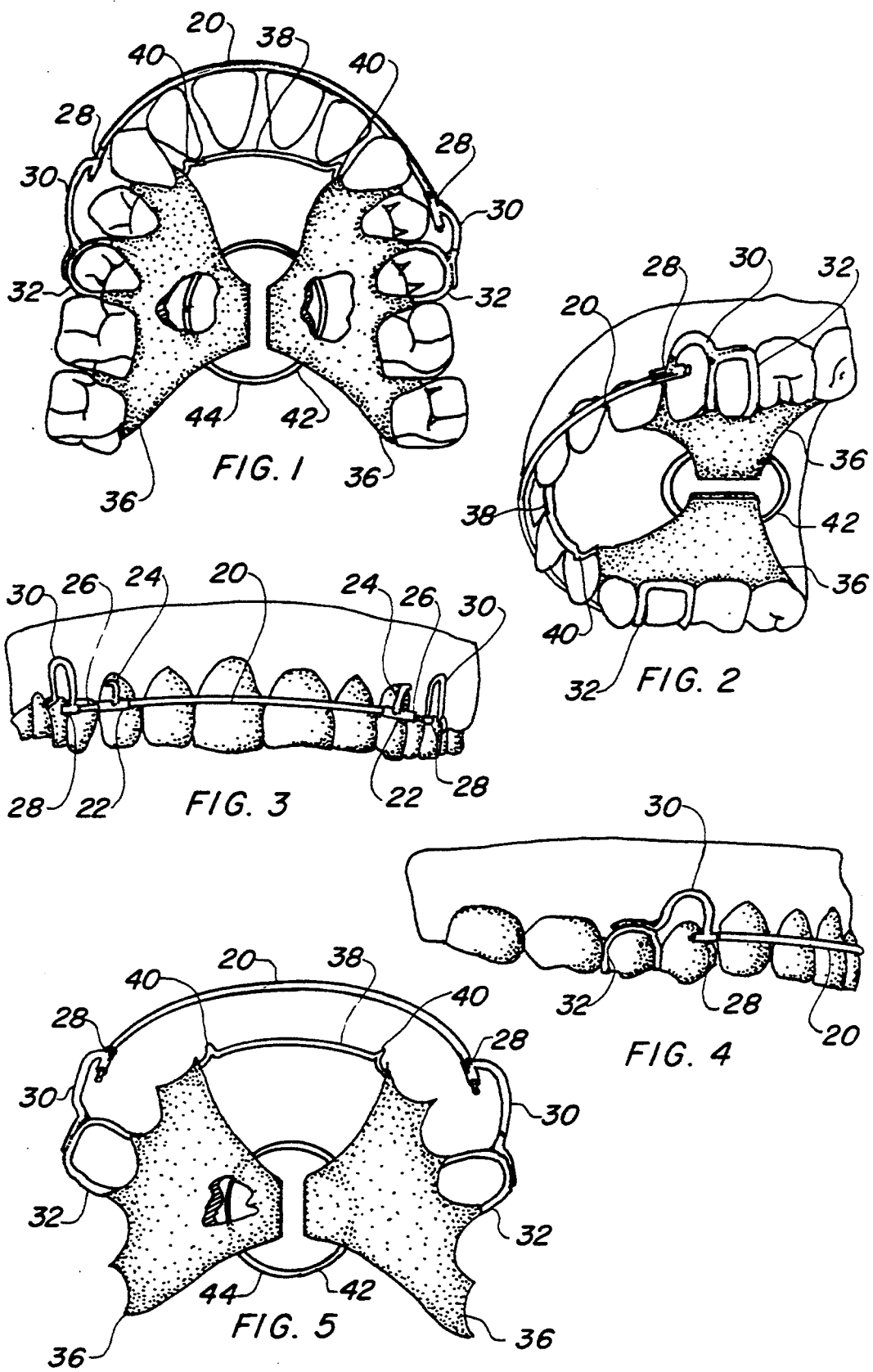

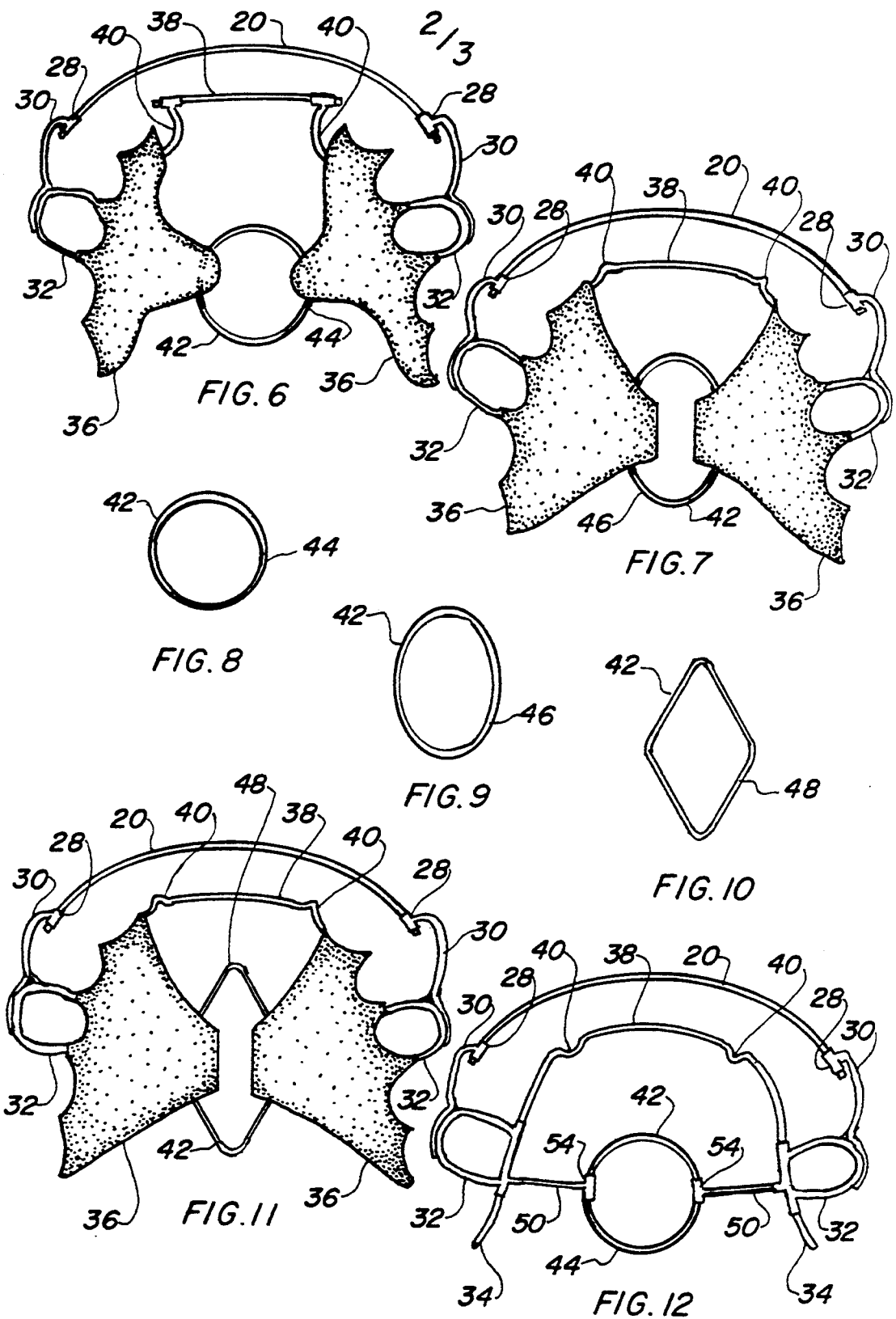

REMOVABLE ORTHODONTIC APPLIANCE

TECHNICAL FIELD

This invention relates to improvements in orthodontic appliances in general, more particularly to removable appliances that straighten teeth and also hold teeth in position after correction.

BACKGROUND ART

Previously, many types of orthodontic appliances have been used in endeavoring to provide an effective means for producing straight teeth in a persons mouth. In the past, removable appliances have employed a resilient arch wire around the labial side of the teeth and another contiguous with the teeth on the lingual side. The above wires are permanently attached to a clasp, or the like, that are secured to the midregion teeth on each side. Further, an expansion plate or wire is disposed across the roof of the mouth and by physically adjusting each wire, a force is placed upon the teeth in such a manner as to reposition individual teeth into the desired position.

Feb. 6, 1987 Harry W. Tepper filed an application for a removable orthodontic appliance which was abandoned in favor of a continuation-in-part application issuing a U.S. Pat. No. 4,976,614. The instant application is an improvement of this patented device by the same inventor with the improvement consisting of the use of a compressible tension bridge positioned within a wearers palatal arch replacing the transverse wire arch structure that presently has a sinuous configuration both of which utilize the so-called shape memory metal. The unique physical and temperature responsive characteristics of this metal is that when the temperature is above a specific transitional range it has the propensity to return to its original shape. Below this range the metal is in a martensitic state which is pliable and easily formed. Above the transitional range the metal reverts to an austenitic state gaining strength seeking to return to its original configuration. This type of shape memory alloy was earlier disclosed in its basic form in the following U.S. Patents:

| U.S. Pat. No. | Inventor | Issue Date |
| --- | --- | --- |
| 3,174,851 | Buehler et al | Mar. 23, 1965 |
| 3,351,463 | Rozner et al | Nov. 7, 1967 |

The application of this metal, particularly in the use of a radially compressible bridge, has not been employed by prior art relative to the improvements in the instant invention, however, the following U.S. Patents are considered related:

| U.S. Pat. No. | Inventor | Issue Date |
| --- | --- | --- |
| 4,976,614 | Tepper | Dec. 11, 1990 |
| 4,468,196 | Keller | Aug. 28, 1984 |
| 4,433,956 | Witzig | Feb. 28, 1984 |
| 4,424,031 | Dahan | Jan. 3, 1984 |

U.S. Pat. No. 4,976,614 issued to the present inventor discloses a removable orthodontic appliance upon which the instant improvement is based. The improvement utilizes a pair of arch wires on the labial and lingual side of the front teeth with a pair of clasps attached to the midregion teeth, as previously taught. A pair of structural braces and a radially compressible tension bridge are added, both being new and not considered in the inventors previous patent, making a new and novel combination.

Keller in U.S. Pat. No. 4,468,196 employs a single arch wire attached to a selected molar on each side of the jaw. The arch wire is covered by a hardenable material in which an optional buccal wire is provided on the outer surface of the front teeth.

Witzig, in Pat. No. 4,433,956, corrects class II malocclusions using acrylic anterior segments over the front teeth and an expandable screw connected to a similar posterior segment over the mid-range teeth. The appliance is mechanically expanded in stages to maximize the utilization of corrective lower jaw movements which result from the anchoring of the device in the upper mouth.

Pat. No. 4,424,031 of Dahan anchors his appliance on opposed molars with a fluted tube-like element. Force conveying means enter each element through a lengthwise groove and is locked in place. This element consists of a facial arc and moves a radial direction relative to the tube-like element forcing the anchored teeth radially.

DISCLOSURE OF THE INVENTION

The inventor's previous Pat. No. 4,976,614 provided bold steps in the advancement of orthodontic correction of malocclusions and retention of teeth after correction, particularly in the removable appliance discipline. The greatest gain was in the time required to accomplish the desired repositioning being only a number of months, as the appliance was self-sustaining and continually yielded a tensional force upon the teeth. Prior to this invention it was customary to leave the device in the mouth for long periods of time, actually several years, and periodically adjust the tension on the wires as required to force the movement of the teeth into the required position. If the forces applied to the teeth are to extensive, the root of the effected tooth may be pathologically loosened. Conversely, if the tension is prematurely decreased and the position does not change, the time required to make the correction is lengthened before the teeth are moved into the final adjusted position. Actually, the movement of the teeth may be required to be in either the posterior or anterior direction and individual teeth may require rotation in distal or medial direction relative to a known axis.

It was discovered that the inventor's previous apparatus accomplished the desired correction, however, the transverse palatal wire arch structure lacked complete flexibility in directive forces. It is, therefore, a primary object of the invention to improve this orthodontic appliance by replacing the palatal arch device, which consists of a flexible wire made of a shape memory alloy formed into a sinuous configuration. In its place, a full or partial loop of the same wire is utilized. While this may appear on the surface to be trivial and insufficient by itself to merit new and novel structure and utility, this is not the case, as the use of a radial bridge or loop in various external formations yields a greatly improved source of controlled tension. A full or partial loop of wire, particularly using the shape memory alloy, produces expansive forces when compressed that have a repeatable and very predictable force versus deflection characteristics. Further, the loop may be easily varied in its overall diameter or in the size of the primary wire when initially formed. The improvement, therefore, permits controlled forces not only laterally but longitudinally, greatly expanding its flexibility.

Further, the original palatal arch device was formed as a periodic structure having cyclic variations defined by long sides joined by transverse end segments with each long side paired together with a heat shrinkable plastic sleeve. The arch device, which was in an accordian-like configuration, received the heat shrink tubing and was heated to contract and compress the arch to the desired extent suitable for fitting between the small tubing sections. It is obvious that this structure, while ultimately accomplishing the desired result, is somewhat complicated and labor intensive to make and difficult to predict its functional capabilities. These drawbacks are completely overcome by the use of the improvement thus presented.

An important object of the invention is directed to the perceived comfort of the patient, as the prior accordian-like arch device with a number of shrink tubing sleeves, has been replaced by a simple full or partial loop of metal in one configuration or the other according to its need. It may be appreciated, particularly by the user, that the original bridge with its multiplicity of bends and connecting pieces of shrink tubing would be uncomfortable and hard to clean as the tubing is open on each end and becomes a receptacle for food particles and the like. The simplicity of the improvement and its miniaturization in size produces a much more comfortable appliance, as the roof of the mouth is an area that is in direct contact with the tongue and any foreign object is disconcerting, particularly one that is large and complicated.

Another object of the improvement is the ease of manufacture of the loop in its full or partial configuration. The preferred embodiment utilizes a full loop of shape memory alloy wire with the wire formed around a mandrel and the ends butting together and attached by acrylic wings. The second embodiment is exactly the same except instead of connecting the loop with molded palatal wings, the loop is captured and held by a pair of transversely opposed wire brace extensions, with the loop remaining unchanged. In either event, the loop may be varied in shape, such as round, elliptical, diamond, etc., each applying a different amount of force when compressed or extended. The diversification in shape allows the dental practitioner to pre-select the optimum force angle and magnitude required to permit the appliance to correct the patient's malocclusion.

It should be noted that the third embodiment uses the same basic loop, except it is cut into an arch and a number of them are used in concert. The purpose of this embodiment is to reshape the pliable alveolar boney process in which the roots of the teeth are supported. In effect, the invention can move teeth without actually touching the crowns of the teeth themselves. In the traditional method of correcting malocclusions, pressures are applied to the crowns of the teeth to preclude osteoblastic and osteoblastic all ear bone cell changes within the alveolar bone, which can be painful and injurious to these supporting structures. However, when the teeth are moved by the reshaping process, the long axises are automatically directed to apply forces to the basal bone of the cranium. The masticatory are directed to the proper foundation support as determined by the so-called "curve of Wilson". The "curve of Spee" involves the position of the crowns of the teeth when the dentition is viewed from the lateral aspect. The "curve of Wilson" involves the crowns of the teeth when the dentition is viewed from a frontal aspect. These two curves are common knowledge in gnathology. When the long axis of the teeth are improperly positioned, pathology is likely to happen. Furthermore, relapses of the corrected malocclusions are less likely to occur when the teeth are in their proper positions. The improvement thus presented, therefore, accomplishes the desired results in each embedment according to the actual need of the individual patient.

Still another object of the improved invention corrects the major cause of the problem as a complete system developed by the inventor utilizes a tongue thrust appliance, U.S. Pat. No. 5,052,409, that reprogram the tongue correcting tis position and function and the instant orthodontic appliance corrects the malocclusion or other muscle abnormality. The removable nature of the appliance permits correction in a considerably shorter time than present methods used by most orthodontists, and precludes relapse.

These and other objects and advantages of the present invention will become apparent from the subsequent detailed description of the preferred and other embodiments, also the appended claims, further taken in conjunction with the accompanying drawings.

BRIEF DESCRIPTION OF THE DRAWINGS

FIG. 1 is a plan view of the preferred embodiment viewed in the inverted position, including the patient's teeth indicating their relationship to the invention.

FIG. 2 is a perspective view of the preferred embodiment viewed from beneath, including the patient's teeth.

FIG. 3 is a front view of the preferred embodiment, including the patient's upper set of teeth.

FIG. 4 is a right side view of the preferred embodiment, including the patient's upper set of teeth.

FIG. 5 is a plan view of the preferred embodiment viewed in the inverted position and removed from the wearers mouth.

FIG. 6 is an inverted plan view of the preferred embodiment with a different palatal wing configuration.

FIG. 7 is an inverted plan view of the preferred embodiment with a different palatal wing and loop configuration.

FIG. 8 is a plan view of the radial loop in the circular configuration completely removed from the invention for clarity.

FIG. 9 is a plan view of the radial loop in the elliptical configuration completely removed from the invention for clarity.

FIG. 10 is a plan view of the radial loop in the diamond shaped configuration completely removed from the invention for clarity.

FIG. 11 is an inverted plan view of the preferred embodiment with a different palatal wing configuration and lop configuration.

FIG. 12 is an inverted plan view of the second embodiment with palatal wire brace extensions.

BEST MODE FOR CARRYING OUT THE INVENTION

Figure 13:
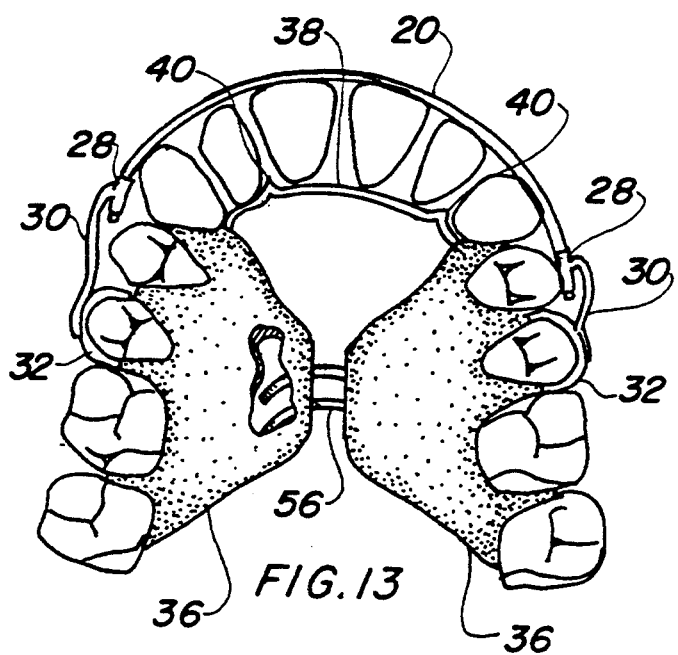
FIG. 13 is a plan view of the third embodiment viewed in the inverted position including the patient's teeth indicating the relationship to the invention.

The best mode for carrying out the invention is presented in terms of a preferred, second and a third embodiment. All three embodiments are primarily designed alike, except for the structural braces and radially compressible tension bridge. In all cases, the invention includes a labial arch wire 20 that is registrable around a patient's upper anterior teeth surfaces. The labial arch wire 20 is made of metal and is substantially rigid, preferably 0.016 inch (0.04 cm) diameter and formed into a curve contiguous with the anterior surface of at least the central, lateral and cuspid teeth. The labial arch wire 20 may be attached at each end with a tubing section 22 that may optionally incorporate a hook 24 for use with resilient band means consisting of dental elastics (not illustrated, but well known in the art) for changing upper and lower jaw relationship in an interior, posterior relationship called class II correction. This option is shown only in FIG. 3. A short interconnecting wire segment 26 leading to a small base tube 28 is required. In any event, each base tube 28 is connected to a partially open side loop 30 by soldering or the like. Each side loop 30 is not closed so that it may be compressed or expanded in the anterior-posterior direction, thereby adjusting the arch form. The posterior end of each side loop 30 is joined to a clasp 32 that is removably engagable to midregion teeth on each side of a patient's mouth securing the labial arch wire 20 on each end. Each clasp 32 specifically encircles the second pre-molar or bicuspid so that maximum leverage advantage is obtained.

Figure 15:
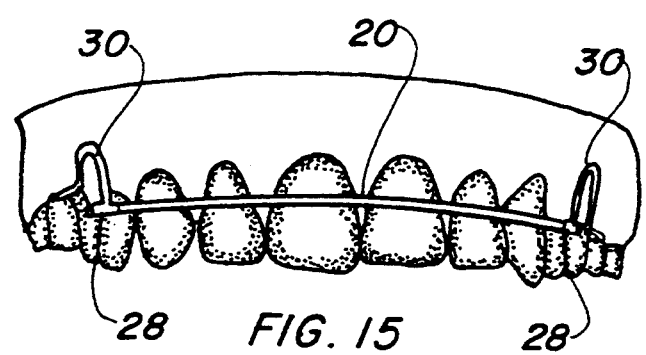
FIG. 15 is a front view of the third embodiment, including the wearers upper set of teeth.

In the preferred embodiment, illustrated in FIGS. 1 through 7, and 11, and also the third embodiment, illustrated in FIGS. 13 and 15, the clasps 32 are secured by a pair of structural braces, or brace extensions, in the form of molded palatal wings 36 with each wing contiguously embracing opposed pre-molar and molar teeth adjacent to the patient's gingival surface. The wings 36 are made of conventional mono-methylate which sets quickly under ultraviolet light, or any other material suitable for the purpose, all of which is well known in the art. The configuration of each wing 36, best illustrated in FIGS. 1 and 5, is such that a predetermined distance is maintained between the extended end of each wing opposite the clasps 32. This gap permits the dental practitioner to select and physically limit the amount of lateral movement of the appliance between the opposed pre-molar and molar teeth. A gap of from 1 millimeter to 8 millimeters is optimum and its use physically maintains this minimum gap as the wings come together and physically touch each other in the minimum orientation.

Lingual arch wire means, of spring material, having securing means takes the form of a lingual arch wire 38 that contains a similar but smaller radius of curvature than the labial arch wire 20. This lingual arch wire 38 engages the posterior surfaces of the central, laterals and cuspids and includes a U-shaped loop 40 near each end for adjustment. The securing means in this embodiment takes the form of embedding the ends in the molded wings 36.

Preferably this lingual arch wire 38 is made of the so-called memory metal, or shape memory alloy, and seeks to form an ideal arch geometry with linear force characteristics throughout its bend radius. This memory metal is of nickel titanium alloy, generally known as Nitinol and sold commercially under the trademark "Tinel" as a shape memory alloy by Raychem Corp. of Menlo Park, Calif.

This type of material has unique physical and temperature responsive properties, in that it has selectable transition temperature ranges dependent upon the contents of the alloy. Below the transition temperature range the metal is in a martensitic state, in which it is soft and can be deformed. Above the transition range the metal reverts to an austenitic state in which it regains strength and seeks to return to a predetermined shape, which in this case, is a particular curve for the wire. The memory metal also can be greatly distorted without exceeding its yield point. A memory wire, as used here can, for example, be tied in a knot without assuming a permanent set. Thus permanent distortion resulting from deformation during manufacture is not a problem. In returning to its memory shape a spring force is derived from the memory characteristic of the metal, as well as the shape distortion. Consequently, the spring forces exerted are light but substantially uniform over a range, and do not vary substantially as the arch changes position toward the desired orientation. This application of a substantially uniform force throughout a wide excursion range gently but relatively rapidly urges teeth into a selected position. A typical high spring material used for dental applications is different, in that it exerts a very high force when the adjustment is first made, but thereafter the force rapidly decreases as position its relative changes.

A specific novelty of the improved invention is in the use of radial compressible tension bridge means which, in the preferred and second embodiment, is in the form of a continuous radial loop 42. This loop 42 may be a round circular wire ring 44, as illustrated in FIGS. 1, 3, 5 through 7, 8 and 12, having the converging ends touching together to form the ring. The wire utilized is the above described shape memory alloy and the ring has an outside diameter of from 15 to 30 millimeters and the wire itself is from 0.40 millimeters to 0.90 millimeters thick. The same wire may be formed into an elliptical shaped oval ring 46, as shown in FIGS. 7 and 9, or a diamond shaped ring 48, having the ends contiguously embracing each other and forming an obtuse angle symmetrical with the balance of the wire thus forming the diamond shape. This embodiment is shown in FIGS. 10 and 11.

While these three loop shapes, round 44, elliptical 46 and diamond 48 are described as being made of the above discussed memory metal, full hard austenitic stainless steel or a thermoplastic filament may be substituted to optimize the particular characteristic of this alternate material giving the dental practitioner a wide range of choices that develop the most favorable appliance for the specific application.

In any event, the continuous radial loop 42 in all its varieties is captivated by the molded palatal wings 36 and is superposed within the patient's palatal arch region, as depicted in FIGS. 1, 2, 5 through 7, and 11. Each wing 36 completely surrounds at least one portion of the loop 42, one of which contains the converging ends touching together thereby eliminating the necessity of attaching the ends together beforehand. When the loop 42, in any of its configurations, is embedded in the wings 36, it is compressed laterally or longitudinally, according to the desired force displacement which either places the force outwardly or is drawn together inwardly upon the midregion teeth, specifically the second pre-molar and bicuspid on each side attached to the appliance by the clasps 32. Any other specific force direction or combination thereof may be achieved by the use of this radial loop 42. Specifically, the loop 42 has the propensity to return to its original shape exerting a continual and persistent linear force in the opposite direction or deformation until deformation ceases and the loop 42 is at rest in its original form. The appliance then becomes the retainer in its simple form as the forces are now equalized and resist further movement in the opposite direction. It is easily seen that full control of the force orientations and amplitude is achieved by this novel arrangement as the type, size, and shape of the material is alterable achieving a completely versatile method of relocating teeth. All adjustments have been previously made in the laboratory in the manufacture of the appliance. Chair adjustments are none or minimal.

While the preferred embodiment is illustrated in FIGS. 1 through 11, the second embodiment is depicted singly in FIG. 12 and differs only in the method of attaching the clasps 32 to the lingual arch wire 38 and radial loop 42. The molded palatal wings 36 are replaced by wires to achieve the desired interconnection. To insure rigidity of the appliance to the teeth, a posterior lingual extension 34 is attached to each clasp 32 bearing against at least one molar on each side. The attachment is made by the use of hollow connecting tubing sections 50 that receive the extension 34 on one end and the lingual arch wire 38 on the other. The clasp 32 is butted into the connecting section 50 and soldered or brazed, as shown in FIG. 12. A loop retaining wire 52 connects the loop 42 to the connecting section 50 in the same manner and a loop retaining sleeve 54 is slipped over the loop 52 and the entire assembly soldered or brazed by methods well known in the art. The retaining wire 52 is formed to match the palatal arch region of the patient's mouth and the butting ends of the loop 42 are covered by the sleeve 54 that retains the loop, by crimping, to assure the integrity of the loop material. It should be noted that any of the loop 42 shapes, such as round 44, elliptical 46, or diamond shaped 48 work equally well in this embodiment and may be utilized with impunity. The balance of this second embodiment is unchanged from that previously presented and the function is the same.

Figure 16:
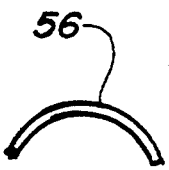
FIG. 16 is a plan view of the radial arc completely removed from the invention for clarity.
Figure 17:
FIG. 17 is a plan view of another configuration of the radial arc completely removed from the invention for clarity.
Figure 18:
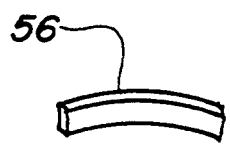
FIG. 18 is a plan view of a thermoplastic configuration of the radial arc completely removed from the invention for clarity.
Figure 19:
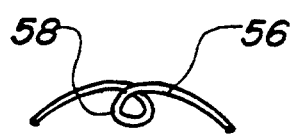
FIG. 19 is a plan view of a spring configuration of the radial arc completely removed from the invention for clarity.

The third embodiment, shown in FIGS. 13 through 19, is again the same as the preferred, except in the radially compressible tension bridge which takes for form of at least one structural radial arc 56. This arc 56 is basically in the same shape as the round circular wire ring 44, except it is only a partial section. It may be made by cutting the ring into sections, as the material is exactly the same including the shape memory alloy, fully hard austenitic stainless steel and thermoplastic filament. It should be noted, however, that the wire thickness and ring diameter may be different and the thermoplastic member may be configured as a ribbon, depicted in FIG. 18, or as a round filament, illustrated in FIGS. 16 and 17. In any case, the arc 56, including all of it's varying materials, may be formed with a spring-like looped center 58, shown alternately in FIG. 19, to achieve a much greater torsional force.

Figure 14:
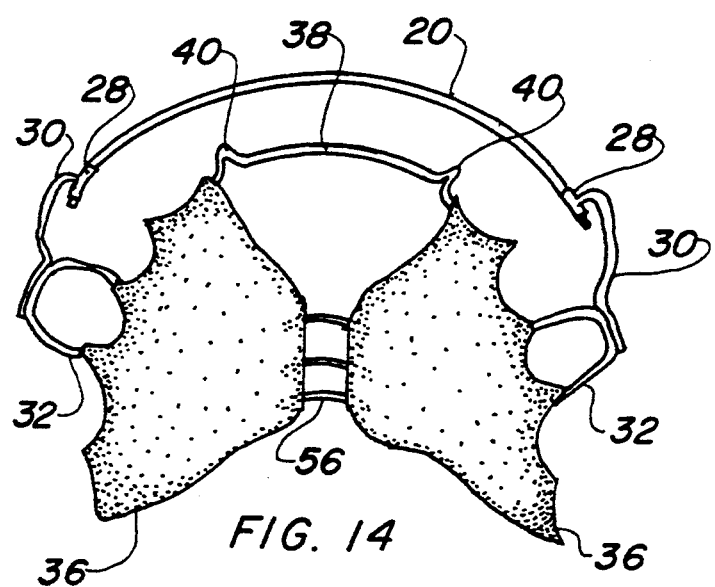
FIG. 14 is a plan view of the third embodiment, except with three radial arc's and removed from the wearers mouth.

It will be noted that any number of arc's 56 may be used from a single piece to as many as required, as an example, two are shown in FIG. 13 and three in FIG. 14. While the basic structure is the same as the preferred embodiment, the utility changes somewhat as a compound force direction may be obtained. The angularity of the teeth, including its roots, may be repositioned with this embodiment to maintain the original angle and basal bone relationship, as previously described. The arc's 56 may be angularly disposed within the wing 36 material, therefore, not only will the appliance spread or retract the teeth, it may now retain or change the angularity as required for optimum relocation. The dental practitioner now has the ability to locate the arc's 56 at the desired angle and change the quantity and deflection pressure almost infinitely.

Figure 20:
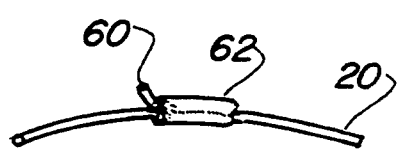
FIG. 20 is a partial isometric view of the individual tooth straightening arm completely removed from the invention for clarity.
Figure 21:
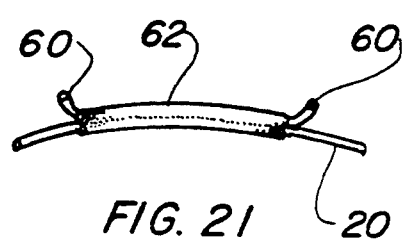
FIG. 21 is a partial isometric view of the dual tooth straightening arm completely removed from the invention for clarity.

FIGS. 20 and 21 illustrate a lever wire 60 of the memory metal that may be optionally attached to the labial arch wire 20 with shrink tubing 62 to serve as a lever to provide a specific force to bear against an individual tooth at a region and in a direction needed to rotate or pivot the tooth into alignment.

While the invention has been described in complete detail and pictorially shown in the accompanying drawings, it is not to be limited to such details, since many changes and modifications may be made in the invention without departing from the spirit and scope thereof. Hence, it is described to cover any and all modifications and forms which may come within the language and scope of the appended claims.

What is claimed is:

1. An improved removable orthodontic appliance for straightening and retaining teeth comprising;
   a labial arch wire registrable about anterior teeth surfaces to define a limit position, the labial arch wire being of rigid material;
   a pair of clasps removably engagable to midregion teeth on opposite sides of the mouth and secured to the labial arch wire at each end thereof;
   a pair of molded palatal wings, each contiguously embracing opposed pre-molar and molar teeth and adjacent gingival surfaces each connectably joined to a clasp forming a structural union therebetween;
   lingual arch wire means of spring material including securing means attached at each end to the wings; and
   a continuously butted radial loop embeddably joined to each of the palatal wings defining a bridge superposed within a patient's palatal arch region having a predetermined distance between each wing, with the loop possessing a propensity to return to its original shape exerting a continual and persistent linear force in the opposite direction of deformation, as the loop is compressed laterally, midregion teeth are forced apart from the loop until the deformation ceases and the loop is at rest in its original form, conversely when the loop is compressed longitudinally, a patient's midregion teeth are drawn together until the loop is restored to its basic shape.

2. The orthodontic appliance as recited in claim 1 wherein the labial arch wire includes side loops adjacent to the clasps, the side loops being open for changing the position of the labial arch wire in the anterior-posterior direction, and wherein the appliance further includes a posterior extension extending from the clasp and engagable to at least one posterior tooth on each side, also the clasps are mountable on a midregion bicuspid to provide a maximum of leverage advantage, and the lingual arch wire means further comprise a memory metal alloy wire and wherein the appliance further comprises resilient band means and hooks on the labial arch wire, the resilient bands intercouple the hooks to increase the degree of arch of the labial arch wire.

3. The orthodontic appliance as recited in claim 1 wherein said predetermined distance between each wing is from 1 millimeter to 8 millimeters permitting a dental practitioner to select and physically limit the amount of lateral movement of the appliance between the opposed premolar and molar teeth.

4. The orthodontic appliance as recited in claim 1 wherein said continuous radial loop further comprises a round circular wire ring with converging ends touching together within the palatal wings.

5. The orthodontic appliance as recited in claim 4 wherein said circular wire ring has a diameter in the range from 15 millimeters to 30 millimeters, and the wire ring has a thickness from 0.40 millimeters to 0.90 millimeters.

6. The orthodontic appliance as recited in claim 1 wherein said continuous radial loop further comprises an elliptical shaped oval ring with converging ends touching together within the palatal wings.

7. The orthodontic appliance as recited in claim 1 wherein said continuous radial loop further comprises a full hard austenitic stainless steel wire generating the continual linear force exerted by the loop upon the wings.

8. An improved removable orthodontic appliance for straightening and retaining teeth comprising;
 a labial arch wire registrable about anterior teeth surfaces to define a limit position, the labial arch wire being of rigid material;
 a pair of clasps removably engagable to midregion teeth on opposite sides of the mouth and secured to the labial arch wire at each end thereof;
 a pair of molded palatal wings, each contiguously embracing opposed pre-molar and molar teeth and adjacent gingival surfaces, each connectably joined to a clasp forming a structural union therebetween;
 lingual arch wire means of spring material including securing means attached at each end to the wings; and
 a continuous radial loop embeddably joined to each of the palatal wings defining a bridge superposed within a patient's palatal arch region having a predetermined distance between each wing, with the loop possessing a propensity to return to its original shape exerting a continual and persistent linear force in the opposite direction of deformation, as the loop is compressed laterally, midregion teeth are forced apart from the loop until the deformation ceases and the loop is at rest in its original form, conversely when the loop is compressed longitudinally, a patient's midregion teeth are drawn together until the loop is restored to its basic shape,
 said continuous radial loop further comprises a diamond shaped ring having a first end and a second end with the first end contiguously embracing the second end, also said loop formed with symmetrical obtuse angles in a diamond shape.

9. An improved removable orthodontic appliance for straightening and retaining teeth comprising;
 a labial arch wire registrable about anterior teeth surfaces to define a limit position, the labial arch wire being or rigid material;
 a pair of clasps removably engagable to midregion teeth on opposite sides of the mouth and secured to the labial arch wire at each end thereof;
 a pair of molded palatal wings, each contiguously embracing opposed pre-molar and molar teeth and adjacent gingival surfaces, each connectably joined to a clasp forming a structural union therebetween;
 lingual arch wire means of spring material including securing means attached at each end to the wings; and
 a continuous radial loop embeddably joined to each of the palatal wings defining a bridge superposed within a patient's palatal arch region having a predetermined distance between each wing, with the loop possessing a propensity to return to its original shape exerting a continual and persistent linear force in the opposite direction of deformation, as the loop is compressed laterally, midregion teeth are forced apart from the loop until the deformation ceases and the loop is at rest in its original form, conversely when the loop is compressed longitudinally, a patient's midregion teeth are drawn together until the loop is restored to its basic shape,
 said continuous radial loop further comprises a shape memory alloy wire formed as a loop below a specific temperature and returning to its original shape when the temperature is raised due to martensitic transformation amplifying the continual linear force exerted by the loop upon the wings.

10. An improved removably orthodontic appliance for straightening and retaining teeth comprising;
 a labial arch wire registrable about anterior teeth surfaces to define a limit position, the labial arch wire being of rigid material;
 a pair of clasps removably engagable to midregion teeth on opposite sides of the mouth and secured to the labial arch wire at each end thereof;
 a pair of molded palatal wings, each contiguously embracing opposed pre-molar and molar teeth and adjacent gingival surfaces, each connectably joined to a clasp forming a structural union therebetween;
 lingual arch wire means of spring material including securing means attached at each end to the wings; and
 a continuous radial loop embeddably joined to each of the palatal wings defining a bridge superposed within a patient's palatal arch region having a predetermined distance between each wing, with the loop possessing a propensity to return to its original shape exerting a continual and persistent linear force in the opposite direction of deformation, as the loop is compressed laterally, midregion teeth are forced apart from the loop until the deformation ceases and the loop is at rest in its original form, conversely when the loop is compressed longitudinally, a patient's midregion teeth are drawn together until the loop is restored to its basic shape, said continuous radial loop further comprises a thermoplastic filament generating the continual linear force exerted by the loop upon the wings.

11. An improved removable orthodontic appliance for straightening and retaining teeth comprising;
- a labial arch wire registrable about anterior teeth surfaces to define a limit position, the labial arch wire being of rigid material;
- a pair of clasps removably engagable to midregion teeth on opposite sides of the mouth and secured to the labial arch wire at each end thereof;
- a pair of transversely opposed palatal wire brace extensions having a first end and a second end with each first end connected to each clasp, each extension formed of a rigid structural wire;
- lingual arch wire means of spring material including securing means attached at each end to the brace extensions; and
- a continuously butted radial loop attachably joined to the second end of each extension defining a bridge superposed within a patient's palatal arch region with the loop possessing a propensity to return to its original shape exerting a continual and persistent linear force in the opposite direction of deformation, as the loop is compressed laterally, the patient's midregion teeth are forced apart from the loop until the deformation ceases and the loop is at rest in its original form, conversely when the loop is compressed longitudinally a patient's midregion teeth are drawn together until the loop is restored to its basic shape.

12. The orthodontic appliance as recited in claim 11 wherein the labial arch wire includes side loops adjacent to the clasps, the side loops being open for changing the position of the labial arch wire in the anterior-posterior direction, and wherein the appliance further includes a posterior extension extending from the clasp and engagable to at least one posterior tooth on each side, also the clasps are mountable on a midregion bicuspid to provide a maximum of leverage advantage, and the lingual arch wire means further comprise a memory metal alloy wire and wherein the appliance further comprises resilient band means and hooks on the labial arch, where the resilient bands intercouple the hooks to increase the degree of arch of the labial arch wire.

13. The orthodontic appliance as recited in claim 11 wherein said continuous radial loop further comprises a circular wire ring with converging ends touching together and held captivated at each extensions second end.

14. The orthodontic appliance as recited in claim 13 wherein said circuit wire ring has a diameter in the range from 15 millimeters to 30 millimeters, and the wire ring has a thickness from 0.40 millimeters to 0.90 millimeters thick.

15. The orthodontic appliance as recited in claim 11 wherein said continuous radial loop further comprises an elliptical shaped oval ring with converging ends touching together and held captivated by the second end of the extensions.

16. The orthodontic appliance as recited in claim 11 wherein said continuous radial loop further comprises a full hard austenitic stainless steel wire generating the continual linear force exerted by the loop upon the palatal extensions and clasps.

17. An improved removable orthodontic appliance for straightening and retaining teeth comprising;
- a labial arch wire registrable about anterior teeth surfaces to define a limit position, the labial arch wire being of rigid material;
- a pair of clasps removably engagable to midregion teeth on opposite sides of the mouth and secured to the labial arch wire at each end thereof;
- a pair of transversely opposed palatal wire brace extensions having a first end and a second end with each first end connected to each clasp, each extension formed of a rigid structural wire;
- lingual arch wire means of spring material including securing means attached at each end to the brace extensions; and
- a continuous radial loop attachably joined to the second end of each extension defining a bridge superposed within a patient's palatal arch region with the loop possessing a propensity to return to its original shape exerting a continual and persistent linear force in the opposite direction of deformation, as the loop is compressed laterally, patient's midregion teeth are forced apart from the loop until the deformation ceases and the loop is at rest in its original form, conversely when the loop is compressed longitudinally a patient's midregion teeth are drawn together until the loop is restored to its basic shape, said continuous radial loop further comprises a diamond shaped wire having a first end and a second end, with the first end contiguously embracing the second end, also said loop formed with symmetrical obtuse angles in a diamond shape.

18. An improved removable orthodontic appliance for straightening and retaining teeth comprising;
- a labial arch wire registrable about anterior teeth surfaces to define a limit position, the labial arch wire being of rigid material;
- a pair of clasps removably engagable to midregion teeth on opposite sides of the mouth and secured to the labial arch wire at each end thereof;
- a pair of transversely opposed palatal wire brace extensions having a first end and a second end with each first end connected to each clasp, each extension formed of a rigid structural wire;
- lingual arch wire means of spring material including securing means attached at each end to the brace extensions; and
- a continuous radial loop attachably joined to the second end of each extension defining a bridge superposed within a patient's palatal arch region with the loop possessing a propensity to return to its original shape exerting a continual and persistent linear force in the opposite direction of deformation, as the loop is compressed laterally, patient's midregion teeth are forced apart from the loop until the deformation ceases and the loop is at rest in its original form, conversely when the loop is compressed longitudinally a patient's midregion teeth are drawn together until the loop is restored to its basic shape, said continuous radial loop further comprises a shape memory alloy wire formed as a loop below a specific temperature and returning to its original same shape when the temperature is raised due to a martensitic transformation amplifying the continual linear force exerted by the loop upon the palatal extensions and clasps.

19. An improved removable orthodontic appliance for straightening and retaining teeth comprising;

- a labial arch wire registrable about anterior teeth surfaces to define a limit position, the labial arch wire being of rigid material;
- a pair of clasps removably engagable to midregion teeth on opposite sides of the mouth and secured to the labial arch wire at each end thereof;
- a pair of transversely opposed palatal wire brace extensions having a first end and a second end with each first end connected to each clasp, each extension formed of a rigid structural wire;
- lingual arch wire means of spring material including securing means attached at each end to the brace extensions; and
- a continuous radial loop attachably joined to the second end of each extension defining a bridge superposed within a patient's palatal arch region with the loop possessing a propensity to return to its original shape exerting a continual and persistent linear force in the opposite direction of deformation, as the loop is compressed laterally, patient's midregion teeth are forced apart from the loop until the deformation ceases and the loop is at rest in its original form, conversely when the loop is compressed longitudinally a patient's midregion teeth are drawn together until the loop is restored to its basic shape, said continuous radial loop further comprises a thermoplastic filament generating the continual linear force exerted by the loop upon the palatal extensions and clasps.

* * * * *